United States Patent [19]

Riley et al.

[11] 4,279,928

[45] Jul. 21, 1981

[54] METHOD OF LOWERING BLOOD PRESSURE

[75] Inventors: Richard L. Riley, North Wales; George H. Douglas, Malvern; John Yelnosky, Warrington, all of Pa.

[73] Assignee: William H. Rorer, Inc., Fort Washington, Pa.

[21] Appl. No.: 26,161

[22] Filed: Apr. 2, 1979

[51] Int. Cl.³ .................. A61K 31/165; A61K 31/16; A61K 31/33; A61K 31/155

[52] U.S. Cl. .................................. 424/324; 424/244; 424/248.4; 424/250; 424/256; 424/269; 424/270; 424/272; 424/274; 424/304; 424/309; 424/311; 424/319; 424/321; 424/322; 424/326; 544/63

[58] Field of Search .................... 424/244, 248.4, 250, 424/256, 269, 270, 272, 274, 304, 309, 311, 319, 321, 322, 324, 326; 544/63

[56] References Cited

U.S. PATENT DOCUMENTS

| 4,060,635 | 11/1977 | Diamond et al. | 424/304 X |
| 4,088,785 | 5/1978 | Diamond et al. | 424/304 X |
| 4,117,165 | 9/1978 | Diamond et al. | 424/322 |

OTHER PUBLICATIONS

Arznemittel Forschung, 28 (11), 1978, pp. 1433-1480.
Conn, (Ed) Current Therapy, 1977, W. B. Saunders, Philadelphia, pp. 205-221.

Primary Examiner—Anna P. Fagelson
Attorney, Agent, or Firm—Ernest G. Szoke; James A. Nicholson

[57] ABSTRACT

Multiple daily dosing with amidinoureas of the formula

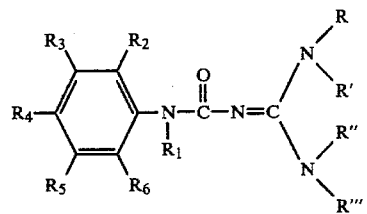

produces a significant and sustained decrease in blood pressure in humans.

14 Claims, No Drawings

METHOD OF LOWERING BLOOD PRESSURE

BACKGROUND OF THE DISCLOSURE

Amidines and related compounds are known to exhibit anti-hypertensive properties as centrally acting anti-hypertensive agents. The overall action on blood pressure by the known amidine hypotensive agents such as clonidine, has been postulated to be the resultant of peripheral and central effects. The determination that the overall effect is a combination of peripheral and central action is based upon animal studies designed to separate these effects. Such studies are described, for example, by Rouot, LeClerk and Wermuth in the *Journal of Medicinal Chemistry*, 1976, Volume 19, No. 8.

Certain amidinoureas have been described as possessing blood pressure lowering effects in recently-issued patents. U.S. Pat. No. 4,088,785 discloses amidinoureas in which an amidino nitrogen is phenyl substituted having blood pressure lowering effects in the spontaneous hyperactive rat in tests done according to the method of Tabei et al, *Clin. Pharm. and Therap.* 11: 269–274, 1970. U.S. Pat. No. 4,117,165 discloses blood pressure lowering activity for amidinoureas in which a urea nitrogen is phenyl substituted and the amidino nitrogens are unsubstituted. In particular, this patent discloses that tests done according to the method of de Champlain et al, *Circulation Research*, xxii: 479 (1968), indicate anti-hypertensive properties for these compounds. U.S. Pat. No. 4,060,635, like U.S. Pat. No. 4,117,165, discloses phenyl substituted amidinoureas in which the phenyl substitution is on a urea nitrogen but which differ from those of U.S. Pat. No. 4,117,165 in that at least one of the amidino nitrogens is also substituted. The compounds are described as useful antidiarrheals without any indication of cardiovascular activity, particularly, hypotensive activity. Compounds of this class are also disclosed, and their properties described, in a monogram appearing in *Arznemittel Forschung* 28 (11), 1433–1480 (1978). At page 1463 of this monogram, it is disclosed that 1-(2'6'-dimethylphenyl)-3-methylamidinourea, a representative member of the compounds with substitution on an amidino nitrogen, also known as lidamidine, has little or no effect on blood pressure over a dose range of 0.1 to 1.0 mg/kg administered intravenously. Thus, from these prior art references, it appears that amidinoureas having phenyl substitution on one of the amidino nitrogens and amidinoureas having phenyl substitution on the urea nitrogen, without substitution on the amidino nitrogen, gave indications of effects on blood pressure in animal tests, whereas amidinoureas which have a phenyl substituent on the urea nitrogen and also substitution on at least one of the amidino nitrogens showed no significant effects on blood pressure in tests on animals. Surprisingly, applicant has now found that a dose-related effect on blood pressure in humans is obtained following administration of 1-(2'6'-dimethylphenyl-3-methylamidinourea in multiple daily doses.

Accordingly, it is an object of this invention to provide a novel method for lowering blood pressure in humans by administering a daily dose of an amidinourea in separate incremental amounts given periodically, thereby to achieve an effective level of active blood pressure lowering substance at the site of activity.

BRIEF DESCRIPTION OF THE INVENTION

In accordance with this invention, amidinoureas are administered to humans in repeated daily doses to lower blood pressure and maintain a lowered blood pressure level by maintaining an effective level of the active substance in the region where activity is exerted.

DETAILED DESCRIPTION OF THE INVENTION

The present invention pertains to a method for lowering blood pressure in humans by administering thereto an amidinourea of Formula I below, over an extended period, in an amount sufficient to produce a hypotensive effect.

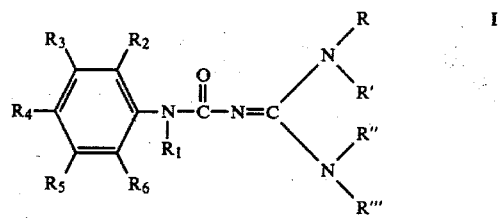

where:
$R_2$, $R_3$, $R_4$, $R_5$ and $R_6$ may be the same or different and are:
hydrogen,
halo,
lower alkyl,
halo lower alkyl,
nitro,
lower alkoxy,
hydroxy,
aryl lower alkoxy,
acyloxy,
cyano,
halo lower alkoxy or,
lower alkyl sulfonyl;
R and R' are hydrogen or lower alkyl;
R" and R''' are hydrogen,
lower alkyl,
lower alkoxy,
lower alkenyl,
cyclo alkenyl,
cyclo alkyl lower alkyl,
cyclo alkyl,
aralkyl,
lower alkynyl,
halo alkyl,
hydroxy alkyl,
alkoxyalkyl,
cyano alkyl,
amino alkyl,
mono- and di- lower alkyl amino alkyl,
carbamoyl alkyl,
mono- and di- carbamoyl alkyl,
carboxy alkyl,
alkoxy carbonyl alkyl,
aralkoxy carbonyl alkyl,
formyl,
acyl,
acyl alkyl,
alkyl sulfonyl or,
aralkyl sulfonyl;

R" and R'" together may form a 5 to 7 atom ring which may include 0 to 2 hetero atoms of N, O or S; $R_1$ is hydrogen or it may be lower alkyl provided at least one of R, R', R" and R'" is other than hydrogen; and, the non-toxic pharmaceutically acceptable salts thereof.

Compounds of this invention which are preferred include those where:

$R_2$, $R_3$, $R_4$, $R_5$ and $R_6$ are hydrogen,
  halo,
  lower alkyl,
  halo lower alkyl,
  nitro,
  hydroxy, or
  lower alkoxy; and,
R' and $R_1$ are hydrogen or lower alkyl; and
R" and R'" are hydrogen,
  alkyl or
  alkoxy; provided R, R', R" and R'" are not all hydrogen at the same time.

The more preferred compounds of this invention include those where:

$R_2$ is hydrogen or lower alkyl;
$R_3$ and $R_5$ are hydrogen,
  hydroxy or
  lower alkoxy;
$R_4$ is hydrogen,
  lower alkyl,
  hydroxy,
  lower alkoxy or
  halo;
$R_6$ is hydrogen,
  lower alkyl,
  nitro,
  alkoxy or
  halo;
R and $R_1$ are hydrogen or lower alkyl; and R' and R" are hydrogen or alkyl; provided R, R', R" and R'" are not all hydrogen at the same time.

The most preferred compounds of this invention are those where:

$R_2$ is hydrogen,
  methyl,
  ethyl,
  chloro or
  bromo;
$R_3$ is hydrogen,
  hydroxy, or
  methoxy;
$R_4$ is hydrogen,
  methyl,
  ethyl,
  hydroxy,
  methoxy,
  chloro or
  bromo;
$R_5$ is hydrogen,
  hydroxy or
  methoxy;
$R_6$ is hydrogen,
  methyl,
  ethyl,
  nitro,
  methoxy,
  ethoxy,
  chloro,
  bromo or
  fluoro;
R and $R_1$ are hydrogen,
  methyl or
  ethyl; and
R' and R" are hydrogen,
  methyl,
  ethyl,
  propyl,
  i-propyl,
  butyl,
  i-butyl,
  sec-butyl,
  t-butyl,
  methoxy,
  ethoxy,
  propoxy,
  butoxy,
  isopropoxy,
  isobutoxy,
  t-butoxy,
  pentyl,
  hexyl or
  heptyl; provided R, R', R" and R'" are not all hydrogen at the same time.

A special embodiment of this invention comprises compounds which have:

$R_2$-lower alkyl substitution;
$R_2$, $R_6$-dilower alkyl substitution;
$R_2$, $R_6$-lower alkyl, alkoxy substitution,
$R_2$, $R_6$-lower alkyl, halo substitution;
$R_2$, $R_6$-alkyl, nitro substitution;
$R_2$, $R_4$, $R_6$-trilower alkyl substitution, or
$R_2$, $R_4$, $R_6$-lower alkyl, dihalo substitution.

A further special embodiment of this invention comprises compounds which have:

R, R', R" and R'" as hydrogen or lower alkyl substitution provided all are not hydrogen at the same time; or,
R and R' are hydrogen or lower alkyl and R" and R'" are an alkyl or alkoxy group from 3 to 7 carbon atoms.

The compounds of Formula I and the method of preparing them is described in U.S. Pat. No. 4,060,635 and in *Arzneimittel Forschung*, 28 (II), 1433–1480 (1978), the disclosures of which are incorporated herein by reference.

As is known, certain compounds of Formula I can exist in enolized or tautomeric forms or may be obtained as hydrates or in different polymorphic forms. Illustrative of tautomeric forms are the compounds of Formula I wherein R is hydrogen, in which case the compounds may exist in the alternative structural forms shown below:

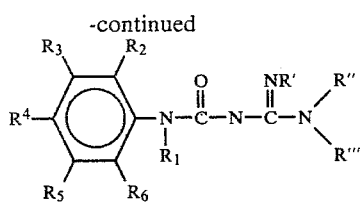

It is understood that the designations of the amidinoureas suitable for use in the practice of this invention are intended to include the compounds specifically named or shown by structure along with the alternative or transient states where such exist. It is also intended to include the pharmaceutically acceptable salts of the amidinoureas designated by Formula I. Such salts include the non-toxic acid addition salts as well as other salts for example, quarternary ammonium salts.

In evaluating the amidinoureas of Formula I for cardiovascular activity, depression of autonomic reflexes is observed following intravenous administration to anesthesized dogs. This depression does not appear to be mediated at the level of the tissue receptors, at autonomic ganglia or at the level of the vascular baroreceptors. The pharmacological spectra of some known antihypertensive agents (clonidine, xylazine, BS-100-141, indoramin, and guanabenz) suggests reduction of efferent sympathetic activity via a depressant effect on sympathetic centers within the medulla oblongata.

Tests indicate that the amidinoureas of Formula I, which are substantially devoid of local anesthetic activity at test doses, preferentially abolish efferent sympathetic activity without a significant effect on vagal reflexes and accordingly, comprises a preferred group of antihypertensive agents. These amidinoureas appear to act primarily at the level of the central nervous system following parenteral administration.

Central administration of amidinoureas of Formula I in anesthesized dogs generally cause hypotension immediately after injection. The 2,6-disubstituted phenyl amidinoureas have maximal cardiovascular reactivity. Substitions with dimethyl, methylchloro, methylbromo, etc., have produced compounds with significant cardiovascular reactivity of varying degrees of duration. Given intravenously, these compounds reduce or abolish efferent sympathetic and vagal reflex activities. After injection directly into the cerebral ventricles, they produce generally similar responses (abolished efferent sympathetic and vagal reflexes) but at doses significantly lower than required when administered i.v.

Preliminary experiments also suggest that hydroxymethylphenyl derivatives also prevent passage through the blood brain barrier.

After i.v. administration of amidinoureas of Formula I, sympathetic responses to carotid artery occlusion and 90° upright tilt are prevented, as with clonidine. Amidinoureas of Formula I also reduce or abolish acetylcholine-induced vasodilation and reflex tachycardia. Tachycardia due to direct stimulation of cardiac β-adrenergic receptors with isoproterenol is not reduced by amidinoureas, indicating that only reflex responses are affected. The amidinoureas exert their hypotensive effects at low doses and short latent periods after injection into the cerebral ventricles indicating an action on autonomic cardiovascular regulatory centers in or around the area of the medulla.

Central and peripheral α-receptor stimulation is obtained after administration of certain amidinoureas, and these effects could be antagonized by α-receptor inhibitors. Central administration of some amidinoureas suppress vagal, as well as sympathetic, reflex activity. Because of compound selectivity with respect to (1) distribution between central and peripheral compartments, and (2) preferential α-sympathomimetic vs. local anesthetic activity, compounds with a central mechanism of action can be selected as a preferred class of potent antihypertensive agents.

The preferred class of amidinoureas for use as hypotensive or antihypertensive agents are the compounds of the formula

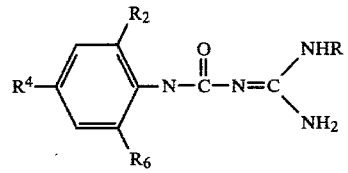

wherein R is lower alkyl, preferably, methyl, ethyl or propyl; or lower alkoxy, preferably, methoxy, ethoxy or propoxy; and $R_2$ and $R_6$ are the same and are lower alkyl, halo or halo lower alkyl; and $R_4$ is hydrogen, lower alkyl, halo, or halo lower alkyl In accordance with this invention, compounds of Formula I, when administered to normotensive humans in single daily doses as high as 180 mg, showed no consistent blood pressure effects. However, when administered in multiple doses of 10, 15, 20, 35 and 60 mg, three times daily, every eight hours for up to seven days, showed consistent dose-related blood pressure lowering effects. Accordingly, these compounds can be used to reduce blood pressure in humans.

The compounds of Formula I, when administered in suitable pharmacological forms, are useful in reducing blood pressure in hypertensive patients or in any situation where it is desired to lower blood pressure and maintain the blood pressure level at lower pressure. The compounds are useful to reduce and maintain lower blood pressure levels when administered in therapeutically-effective amounts in dosage regimens in accordance with the method of this invention. For this purpose, the compounds can be administered by any of the usual routes of administration, but preferably, orally or parenterally so long as the amount of frequency of administration is sufficient to provide the desired blood pressure lowering effect. This effect may be due to the achievement of sustained blood levels of active amidinoureas or amidinourea metabolite, thereby providing a steady supply of the active substance to reach the site of action at effective levels.

While applicant does not wish to be bound by any particular theory, it is believed that the hypotensive effect of the amidinoureas of Formula I are achieved when the compound is continually supplied to the site of action in local concentrations sufficient to maintain effective levels in the region where the activity is exerted, and that this continual supply can be obtained by continuous or periodically repeated dosing whereby blood levels are maintained above a certain minimum concentration. These compounds are readily absorbed into the bloodstream from the gut and are relatively non-toxic. Accordingly, administration by the oral route is particularly preferred.

Orally, these compounds may be administered in tablets, hard or soft capsules, aqueous or oily suspensions, dispersible powders or granules, emulsions, syrups or elixers. The optimum dosage, of course, will depend on the particular compound being used and the type and severity of the condition being treated. In any specific case, the appropriate dosage selected will further depend on factors of the patient which may influence response to the drug; for example, general health, age, weight, etc. of the subject being treated.

Although the optimum quantities for administration of the compounds of Formula I, in accordance with the present invention, will depend on the compound employed and the particular type of condition treated, oral dose levels of preferred compounds when administered to humans in total daily doses of 0.01 to 5 milligrams per kilogram of body weight, given separately, are particularly useful. The preferred dose range is 0.1 to 2 mg/kg/day. Generally, the blood pressure effect can be detected after the second or third dose.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc. in order to provide a pharmaceutically elegant and palatable preparation.

Further, the active amidinourea may be administered alone or in admixture with other agents having the same or different pharmacological properties. The compositions may contain such selected excipients such as inert diluents such as calcium carbonate, lactose, etc; granulating and disintegrating agents such as magnesium stearate, etc.; binding agents such as starch gelatin, etc.; suspending agents such as methylcellulose, vegatable oil, etc.; dispersing agents such as lecithin, etc.; thickening agents such as beeswax, hard paraffin, etc.; emulsifying agents such as naturally-occurring gums, etc.; non-irratating excipients such as cocoa butter, polyethylene glycols, etc.; and the like. Further, in formulating these compounds for every 100 parts by weight of the composition, there may be present between 5 and 95 parts by weight of the active ingredient. The dosage unit form will generally contain between 0.1 mg and about 50 mg of the active ingredient of this invention. The preferred unit dose is between 5 mg and about 15 mg. The compositions may be taken 1 to 8 times daily depending on the dosage unit required.

As already noted, the hypotensive effect of the compounds of Formula I is observed after repeated doses at periodic intervals. Accordingly, the preferred method in accordance with this invention is to administer the active compound at a rate which will produce the desired hypotensive effect. The preferred rate of administration of oral dosage forms is to divide the total daily dose into two or three equal amounts to be administered at equal intervals to suit the convenience of the patient. Other methods such as sustained release or delayed time release tablets or capsules may also be used so long as there is obtained a sustained effective level of the active ingredient sufficient to produce and maintain a decrease in blood pressure.

In a preferred form, the compounds of this invention are prepared for oral administration in either tablet or capsule form depending upon the solubility and capability of the specific amidinourea chosen and the other ingredients. In another preferred form, this invention is practiced by providing an effective amount of an amidinourea of Formula I, generally between about 5 and 10 mg in a single tablet or capsule suitable for oral administration to be administered at least about twice daily at a dose level of 1 to 2 tablets or capsules per dose.

In general, the dosage regimen in carrying out the methods of this invention is that which insures maximum therapeutic response until improvement is obtained and thereafter, the minimum effective level which gives relief. Generally, the daily dose for adults will be between about 5 and 50 mg/day total dose (preferably about 30 mg per day administered in 2 or 3 equal doses at about 8 to 12 hour intervals), bearing in mind, of course, that in selecting the appropriate dosage in any specific case, consideration must be given to the patient's weight, general health, age and other factors which may influence response to the drug.

The dosage amounts used in administering the drug parenterally or by any other route, can be adjusted as necessary to provide and maintain effective blood pressure levels, for example, when the drug is administered directly by intravenous infusion, the rate of infusion can be adjusted to provide blood levels equivalent to those achieved through oral administration. Generally, the drug will be administered orally, though in situations such as malignant hypertension or other emergency situations, i.v. or other forms of administration may be used.

The following examples illustrate the preparation of tablets and capsules which constitute the preferred dosage forms for oral administration of the compounds of Formula I in accordance with the method of this invention and sterile solutions for parenteral administration:

EXAMPLE 1

A batch of homogenous tablets was prepared, each having the following formula:

| Per Tablet | Ingredients | Per 1000 Tablets |
|---|---|---|
| 5 mg | 1-(2',6'-dimethyl phenyl)-3-methyl amidinourea hydrochloride (lidamidine hydrochloride) | 5 gm |
| 100 mg | Microcrystalline, Cellulose | 100 gm |
| 150 mg | Cornstarch | 150 gm |
| 450 mg | Deionized water | 450 gm |
| 10 mg | Hydrogenated Castor Oil | 10 gm |
| 715 mg | | 715 gm |

The following procedure is used to prepare the tablets: 1-(2'6'-dimethylphenyl)-3-methyl amidinourea, cellulose and 100 gm of starch are blended together dry. A paste of the remaining starch is prepared with deionized water in a steamed jacketed pot. The two components are mixed, granulated and passed through a #8 screen then dried in a Fluid Bed Dryer at about 40° C. and again passed through a #14 mesh screen. The composition is then formed into tablets by compressing on a Stokes Rotary Multi-Layer Tablet Press.

EXAMPLE 2

Therapeutic compositions of the invention are prepared by using known techniques for compounding employing either the base or a salt as the active ingredient along with non-toxic excipients chosen in accordance with the particular form and properties desired for the therapeutic composition. Other therapeutic agents such as analgesics, tranquilizers, etc. may be added as desired.

Tablets which can be advantageously used for either remedial or prophylactic treatments for dysmenorrhea ordinarily accompanied by abnormal uterine muscle action, can be provided in a form which provides relief from dysmenorrhea symptoms when taken at a rate of 1 to 2 tablets twice daily containing between about 5 to 10 mg of the active ingredient. An examplary formulation which can be utilized is, for example, the following:

| | |
|---|---|
| 1-(2'6'-dimethylphenyl)-3-methylamidinourea | 5 mg |
| tricalcium phosphate | 200 mg |
| talc | 50 mg |
| magnesium stearate | 10 mg |
| polyvinyl acetate | 40 mg |

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 310 mg.

EXAMPLE 3

A lot of 1,000 tablets each containing 1 g of 1-(2'6'-diethylphenyl)-3-methylamidinourea is prepared from the following types and amounts of ingredients:

| | |
|---|---|
| 1-(2'6'-diethylphenyl)-3-methyl amidinourea hydrochloride | 10 g |
| dicalcium phosphate | 1 kg |
| methylcellulose USP | 75 kg |
| talc | 150 g |
| cornstarch | 200 g |
| magnesium stearate | 10 g |

The active ingredient and dicalcium phosphate are mixed thoroughly and granulated with a 7.5% solution of methylcellulose in water and passed through a #8 screen and air-dried. The dried granules are passed through a #12 screen and combined with the talc, starch and magnesium stearate with thorough mixing after which the composition is compressed into tablets.

EXAMPLE 4

A lot of 2-piece hard gelatin capsules, each containing 5 mg of 1-(2'6'-dimethylphenyl)-3-methyl amidinourea are prepared from the following types and amounts of ingredients (the amounts given are per capsule):

| | |
|---|---|
| 1-(2'6'-dimethylphenyl)-3-methyl amidinourea hydrochloride | 5 g |
| dicalcium phosphate | 500 g |
| talc | 150 g |
| magnesium stearate | 5 g |

The ingredients are mixed thoroughly and filled into capsules which are used for oral administration at the rate of about one every four hours. If desired, slow release forms can be provided or delayed release forms depending on choice of capsules and formulating ingredients.

By analogous methods and employing techniques known to the art, there are prepared formulations suitable for administration of an effective amount of any of the amidinoureas of Formula I. In particular, by analogy of the processes described above, single dose preparations suitable for oral administration can be readily prepared from the following illustrative amidinoureas:

1-(2'-methyl, 4'6'-dichlorylphenyl)-3-methyl amidinourea 1-(2'-chloro, 6'-methylphenyl)-3-amidinourea hydrochloride 1-(2'-methyl, 6'-bromo)-3-amidinourea 1-(2'-methyl, 6'-methoxy)-3-amidinourea hydrochloride 1-(2'-methyl, 6'-ethyl)-3-amidinourea 1-(2'-methyl, 6'-methoxy)-3-methyl amidinourea 1-(2'6'-dimethylphenyl)-3-amidinourea 1-(2'6'-diethylphenyl)-3-amidinourea 1-(2'6'-diethylphenyl)-3-methyl amidinourea 1-(2'6'-dimethylphenyl)-3-methoxy amidinourea 1-(2'6'-diethylphenyl)-3-methoxy amidinourea

EXAMPLE 5

50 g of 1-(2'6'-dimethylphenyl)-3-methylamidinourea hydrochloride, 5 g of propyl p-hydroxybenzoate are dissolved and dilluted to 5000 cc. with twice distilled water after the addition of modified Sorenson buffer solution in an amount sufficient to adjust the pH value to a pH of 6.0. Sodium chloride is dissolved therein in an amount sufficient to render the resulting solution isotonic. The final solution is passed through a bacteriological filter and the filtrate is autoclaved at 120° C. for 15 minutes to yield a parenterally-applicable solution which contains 50 mg of 1-(2'6'-dimethylphenyl)-3-methylamidinourea hydrochloride in 5 cc.

We claim:

1. A method for lowering blood pressure and maintaining a lowered blood pressure in humans which comprises administering multiple doses of an anti-hypertensive compound over a period of time sufficient to establish an effective blood level thereby producing a reduction in blood pressure and thereafter continuing the administration of said anti-hypertensive compound in amounts sufficient to maintain said reduction in blood pressure wherein said anti-hypertensive compound is a compound of the formula:

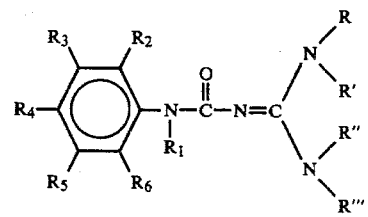

where:

$R_2$, $R_3$, $R_4$, $R_5$ and $R_6$ may be the same or different and are:
hydrogen,
halo,
lower alkyl,
halo lower alkyl,
nitro,
lower alkoxy,
hydroxy,
aryl lower alkoxy,
acyloxy,
cyano,
halo lower alkoxy or
lower alkyl sulfonyl;

R and R' are hydrogen or lower alkyl;

R" and R'" are hydrogen,
  lower alkyl,
  lower alkoxy,
  lower alkenyl,
  cyano alkenyl up to 9 carbon atoms,
  cyclo alkyl lower alkyl,
  lower alkyl,
  cyclo alkyl,
  aralkyl,
  lower alkynyl,
  halo alkyl,
  hydroxy alkyl,
  alkoxy alkyl,
  cyano alkyl,
  amino alkyl,
  mono- and di- lower alkyl amino alkyl,
  carbamoyl alkyl,
  mono- and di- carbamoyl alkyl,
  carboxy alkyl,
  alkoxy carbonyl alkyl,
  aralkoxy carbonyl alkyl,
  acyl,
  acylalkyl,
  alkylsulfonyl or
  aralkyl sulfonyl;
R" and R'" together may form a 5 to 7 atom ring which may include 0 to 2 hetero atoms of N, O or S;
R₁ is hydrogen or lower alkyl; provided at least one of R, R', and R'" is other than hydrogen; and the pharmaceutically-acceptable salts thereof.

2. A method for lowering blood pressure and maintaining a lowered blood pressure in humans which comprises administering multiple doses of an anti-hypertensive compound over a period of time sufficient to establish an effective blood level thereby producing a reduction in blood pressure and thereafter continuing the administration of said anti-hypertensive compound in amounts sufficient to maintain said reduction in blood pressure wherein said anti-hypertensive compound is a compound of the formula:

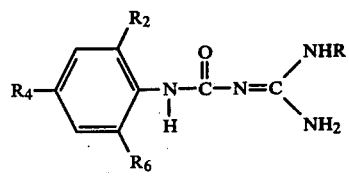

wherein R is lower alkyl, or lower alkoxy; and R₂ and R₆ are the same and are lower alkyl, halo or halo lower alkyl; and R₄ is hydrogen, lower alkyl, halo, or halo lower alkyl; and the pharmaceutically-acceptable salts thereof.

3. The method according to claim 2 wherein the compound is administered in tablet form.

4. The method according to claim 3 wherein the said tablet contains between about 5 and about 30 mg of said compound.

5. A method according to claim 2 wherein R is methyl, ethyl, propyl, methoxy, ethoxy or propoxy.

6. The method according to claim 2 wherein the said compound is 1-(2',6'-dimethylphenyl)-3-methylamidinourea and the pharmaceutically acceptable salts thereof.

7. A method for lowering blood pressure in humans which comprises the administration of multiple doses of an amidinourea sufficient to establish an effective blood level of said amidinourea, thereby inducing a reduction in blood pressure, and, thereafter, continuing the administration of said amidinourea in amounts sufficient to maintain said reduction in blood pressure; wherein said amidinourea is a compound of the formula:

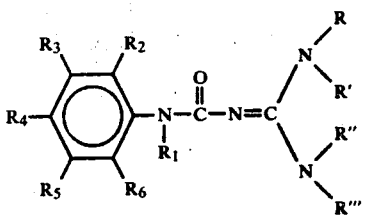

where:
R₂, R₃, R₄, R₅ and R₆ may be the same or different and are:
  hydrogen,
  halo,
  lower alkyl,
  halo lower alkyl,
  nitro,
  lower alkoxy,
  hydroxy,
  aryl lower alkoxy,
  acyloxy,
  cyano,
  halo lower alkoxy, or
  lower alkyl sulfonyl;
R and R' are hydrogen or lower alkyl;
R" and R'" are hydrogen,
  lower alkyl,
  lower alkoxy,
  lower alkenyl,
  cyclo alkenyl up to 9 carbon atoms,
  cyclo alkyl lower alkyl,
  lower alkyl,
  cyclo alkyl,
  aralkyl,
  lower alkynyl,
  halo alkyl,
  hydroxy alkyl,
  alkoxy alkyl,
  cyano alkyl,
  amino alkyl,
  mono- and di- lower alkyl amino alkyl,
  carbamoyl alkyl,
  mono- and di- carbamoyl alkyl,
  carboxy alkyl,
  alkoxy carbonyl alkyl,
  aralkoxy carbonyl alkyl,
  acyl,
  alkylsulfonyl or
  aralkyl sulfonyl;
R" and R'" together may form a 5 to 7 atom ring which may include 0 to 2 hetero atoms of N, O or S;
R₁ is hydrogen or lower alkyl; provided at least one of R, R', R", and R'" is other than hydrogen; and the pharmaceutically acceptable salts thereof.

8. The method according to claim 7 wherein the amidinourea is 1-(2',6'-dimethylphenyl)-3-methylamidinourea and the pharmaceutically acceptable salts thereof.

9. The method according to claim 7 where the compound is administered in tablet form.

10. A method for lowering blood pressure in humans which comprises the administration of a continual supply of an amidinourea sufficient to establish an effective blood level of said amidinourea, thereby inducing a reduction in blood pressure, and, thereafter, continuing the administration of said amidinourea in amounts sufficient to maintain said reduction in blood pressure; wherein said amidinourea is a compound of the formula:

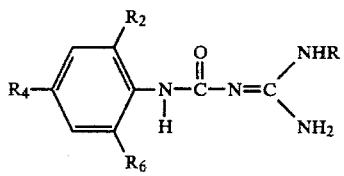

wherein R is lower alkyl, or lower alkoxy; and $R_2$ and $R_6$ are the same and are lower alkyl, halo or halo lower alkyl; and $R_4$ is hydrogen, lower alkyl, halo, or halo lower alkyl; and the pharmaceutically-acceptable salts thereof.

11. The method according to claim 10 wherein the continual supply of amidinourea is provided by a time release capsule.

12. The method according to claim 10 wherein the amidinourea is 1-(2',6'-dimethylphenyl)-3-methyl amidinourea; and the pharmaceutically acceptable salts thereof.

13. A method for lowering blood pressure in humans which comprises administering multiple doses of an anti-hypertensive compound over a period of time sufficient to establish an effective blood level thereby producing a reduction in blood pressure wherein said anti-hypertensive compound is a compound of the formula:

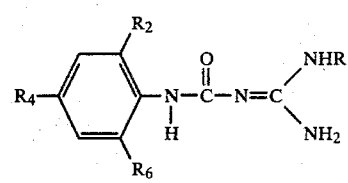

wherein R is lower alkyl, or lower alkoxy; and $R_2$ and $R_6$ are the same and are lower alkyl, halo or halo lower alkyl; and $R_4$ is hydrogen, lower alkyl, halo or halo lower alkyl; and the pharmaceutically-acceptable salts thereof.

14. A method of maintaining lowered blood pressure in humans comprising the administration of multiple doses of an anti-hypertensive compound over a period of time sufficient to establish an effective blood level thereby maintaining a reduced blood pressure wherein said anti-hypertensive compound is a compound of the formula:

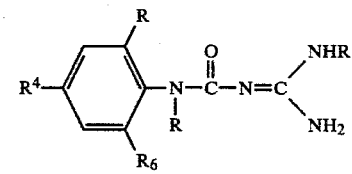

wherein R is lower alkyl, or lower alkoxy; and $R_2$ and $R_6$ are the same and are lower alkyl, halo or halo lower alkyl; and $R_4$ is hydrogen, lower alkyl, halo, or halo lower alkyl; and the pharmaceutically-acceptable salts thereof.

* * * * *